United States Patent [19]

Grenier et al.

[11] Patent Number: 5,003,054
[45] Date of Patent: Mar. 26, 1991

[54] OUABAIN TRIACETATE DERIVATIVE COMPOUNDS

[75] Inventors: Frank C. Grenier; Terry A. Pry, both of Libertyville; Lawrence Kolaczkowski, Vernon Hills, all of Ill.

[73] Assignee: Abbott Laboratories, Abbott Park, Ill.

[21] Appl. No.: 235,267

[22] Filed: Aug. 23, 1988

Related U.S. Application Data

[62] Division of Ser. No. 35,673, Apr. 7, 1987, Pat. No. 4,788,136.

[51] Int. Cl.$^5$ .......................... C07J 19/00; C07J 43/00
[52] U.S. Cl. ......................................... 536/5; 536/6.1; 540/105
[58] Field of Search ..................... 536/6.1, 5; 540/105

[56] References Cited

U.S. PATENT DOCUMENTS

| | | | |
|---|---|---|---|
| 3,654,090 | 4/1972 | Hermasas et al. | 435/7 |
| 4,134,792 | 1/1979 | Boguslaski et al. | 435/7 |
| 4,200,436 | 4/1980 | Mochida et al. | 436/512 |
| 4,298,687 | 11/1981 | Maes | 435/7 |
| 4,350,760 | 9/1982 | Nicolas et al. | 435/7 |
| 4,434,236 | 2/1984 | Freytag | 436/512 |
| 4,551,426 | 11/1985 | Freytag et al. | 435/7 |
| 4,656,143 | 4/1987 | Baker et al. | 436/527 |

FOREIGN PATENT DOCUMENTS

| | | | |
|---|---|---|---|
| 0739638 | 3/1970 | Belgium | 536/6.1 |
| 0115332 | 8/1984 | European Pat. Off. | |
| 0143274 | 6/1985 | European Pat. Off. | |
| 0253270 | 1/1988 | European Pat. Off. | |
| 2000338 | 7/1971 | Fed. Rep. of Germany | 536/6.1 |

OTHER PUBLICATIONS

Megges et al; Chemical Abstracts 76:72755s (1972).
Chemical Abstracts 104:182652K.
Freytag, *Enzyme-Mediated Immunoassay*, edited by T. Ngo and H. Lenhoff, pp. 277-289 (1984).
Freytag et al., *Clin. Chem.*, 30(3):417-420 (1984).
Leflar et al., *Clin. Chem.*, 30(11):1809-1811 (1984).
Leflar et al., "An Automated Immunoassay for Digoxin on the Dupont aca ® Discrete Chemical Analyzer" brochure.
Smith et al., *Biochemistry*, 9:331-337 (1970).

*Primary Examiner*—Ronald W. Griffin
*Assistant Examiner*—Nancy S. Carson
*Attorney, Agent, or Firm*—Robert W. Stevenson; Daniel W. Collins; Thomas M. Breininger

[57] ABSTRACT

A method for performing a diagnostic immunoassay by solid phase separation for digoxin. To a reaction mixture of a test sample and labeled anti-digoxin antibody, which forms a complex of any digoxin present in the test sample, is added a solid phase material having an immobilized ouabain triacetate derivative compound capable of binding any excess labeled antibody. The solid phase material is chosen to rapidly settle whereby a solid and liquid phase is formed. The liquid phase can then be extracted to measure the amount of digoxin-labeled antibody present therein. Ouabain triacetate derivative compounds possess sufficient affinity for anti-digoxin antibodies, and are therefore useful in a solid phase separation based digoxin immunoassay for settling out such antibodies without contributing to undesired background interference. These compounds are also less deleterious to assay performance because of low recognition when leached from the solid phase matrix thereby providing solid phase material with extended shelf life.

2 Claims, No Drawings

OUABAIN TRIACETATE DERIVATIVE COMPOUNDS

This is a division of application Ser. No. 035,673, filed Apr. 7, 1987 now U.S. Pat. No. 4,788,136.

TECHNICAL FIELD

The present invention is directed toward a method and reagents for performing a diagnostic immunoassay for digoxin in biological fluids by a solid-phase separation. The assay employs a solid phase material having an ouabain triacetate compound immobilized thereon. This method is especially suitable for use in automated systems.

BACKGROUND OF THE INVENTION

Many diagnostic immunoassays are known which generally employ the specific binding characteristics that exist between an analyte or protein with a specific antibody tagged with some traceable substituent. One problem which has long been associated with this method is how to remove excess antibody from the biological fluid being tested for analyte in a manner whereby the analyte concentrations can be accurately measured.

Various attempts to remove excess antibody include U.S. Pat. No. 4,298,682 which discloses the absorption of unreacted antibody on a solid phase consisting of a polyacrylamide gel sensitized to the specific antibody.

U.S. Pat. No. 4,551,425 to Freytag et al. discloses another method to remove excess antibody in an immunoassay for digoxin. Here, excess labeled antibody is removed by passing it through an affinity column that has ouabain, an analog of digoxin, immobilized on the solid phase chromatography matrix. The excess antibody is absorbed by the ouabain. The chromatography elute is then examined for the labeled antibody-analyte complex.

While the above can be effective, they are all subject to improvement. In the case of the above-described solid phase separation techniques, the compound immobilized on the solid phase must exhibit sufficient affinity for the labeled antibody to be removed. Ideally, the immobilized compound is irreversibly bound to the solid phase. However, disassociation of the immobilized compound from the solid phase due to leaching can not be avoided. Changes in temperature and microbial contamination are unavoidable and may accelerate this process. This freed material, because of its affinity for antibody, will recognize and complex with labeled antibody producing undesired background interference and reduced assay sensitivity. Disassociation of immobilized compound from the solid phase material is a major contributor to reduced shelf life of the solid phase/immobilized compound complex.

Known compounds useful for immobilization on solid phase material in an immunoassay for digoxin include digoxin and ouabain. These compounds exhibit relatively high affinity for labeled anti-digoxin antibody. However, these same compounds when freed from the solid phase are recognized by the anti-digoxin antibodies; complexing with the antibodies and producing undesired background interference. Loss of relatively small amounts of these compounds adversely effect assay performance. During synthesis or storage of digoxin or ouabain solid phases, disassociation from the solid phase complex will reduce the useful life of the digoxin or ouabain solid phase complex.

Accordingly, there is a need for an improved diagnostic immunoassay by solid phase separation for digoxin which provides a compound exhibiting sufficient antibody binding characteristics when immobilized on the solid phase and which also exhibits low recognition for digoxin when freed from the solid phase material.

SUMMARY OF INVENTION

The present invention relates to a diagnostic immunoassay by solid phase separation for digoxin. The steps of the method comprise (a) forming a reaction mixture of a test sample with a molar excess of labeled anti-digoxin antibody to form a complex of analyte present in the test sample, (b) contacting the reaction mixture with a solid phase material having immobilized thereon a compound having a preferential binding affinity for the labeled anti-digoxin antibody, employed in step (a) which is present in an amount sufficient to complex with any of the excess labeled antibody employed in step (a), (c) allowing the solid phase material and any complex of the solid phase material to settle and form a solid and liquid phase, and (d) measuring the amount of complex present in the liquid phase. Generally, the solid phase material is of sufficient density to rapidly sediment by gravity. Preferably the solid phase material has a sedimentation rate of about 5 seconds to about 2 minutes per centimeter in water and is from about 5 to about 300 microns in diameter. The solid phase material can be formed of any of a variety of materials, preferably, agarose, polystyrene, polyacrylamide, their derivatives or mixtures thereof. Most preferably the solid phase material is Trisacryl ® (Réactifs IBF, F92390 Villeneuve—La-Garenne, France).

This assay may also be conducted in a competitive fashion whereby sample, antibody enzyme and solid phase are mixed simultaneously. After a suitable incubation period the assay is continued as described above at step (c).

The solid phase material has immobilized thereon a compound capable of binding the excess labeled antibody such as a corresponding antigen or chemical analogue. Typically, the labeled antibody is an enzyme labeled antibody. Preferably, the immobilized compound is ouabain triacetate or a derivative thereof having the structural formula:

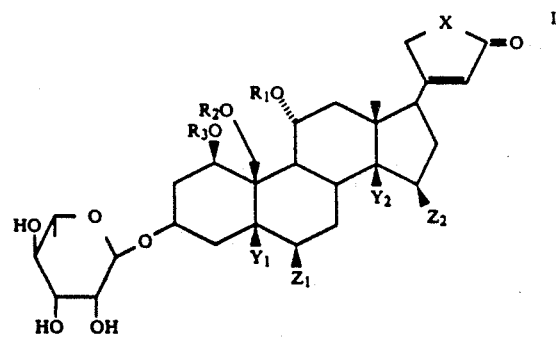

wherein $R_1=R_2=R_3=Ac$, $X=O$, $Y_1=Y_2=OH$, $Z_1=Z_2=H$; or $R_1=R_2=R_3=Ac$, $X=O$, $Y_1=OH$, $Z_1=H$, $Y_2$ and $Z_2=$ a bond connecting the two carbon atoms to which they are attached; or $R_1=R_2=R_3=Ac$, $X=O$, $Y_1$, $Z_1$ and $Z_2=$ a bond connecting the two carbon atoms to which they are attached; or $R_1=R_2=R_3=H$, $X=N$, $Y_1=Y_2=OH$, $Z_1=Z_2=H$. Most preferably, the immobilized compound employed is 1,11,19-tris(acetyloxy)-3-[(6-deoxy-α-L-mannopyranosyl) oxy]-5,14 idhydroxycard-20(22)-enolide, (1β,3β,5βα) having the structural formula:

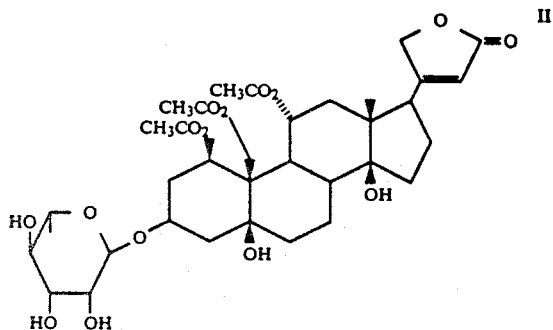

Further, in the preferred embodiment the antibody enzyme conjugate employed is preselected for specific binding to ouabain triacetate rather than digoxin or ouabain.

The present method is particularly adapted for use in automated diagnostic apparatus where centrifugation filtration or column filtration is not possible or practical.

DETAILED DESCRIPTION OF THE INVENTION

The present invention provides for a method whereby any excess labeled anti-digoxin compound employed to identify digoxin can be readily removed to permit accurate measurement of the labeled anti-digoxin retaining which is proportional to the digoxin present in a test sample. The method, as outlined below, is particularly adapted for use in automated systems where traditional purification or removal means are not appropriate, i.e., filtration, centrifugation or filtration columns. More preferably the subject method is employed with the diagnostic immunoassay apparatus TDx ®, a trademark of Abbott Laboratories, for an automated system for the quantitation of therapeutic drug concentrations in serum or plasma based on the method of fluorescence polarization immunoassay.

Generally, the non-competitive method comprises the preparation of a reaction mixture of a biological fluid suspected of containing digoxin with a labeled substance, antibody, capable of complexing with the digoxin. The labeled substance is added to the reaction mixture in a molar excess with regard to the suspected amount of digoxin to be quantified to assure complete complexing thereof.

After an appropriate incubation time, i.e., sufficient time to allow the labeling substance to complex with all the material sought to be quantified, the complex is measured. However, because the labeling substance is employed in a molar excess it is necessary to remove this excess prior to measuring the amount of complex formed.

The subject method is characterized by removing the excess labeled substance by adding a solid phase material having immobilized thereon a compound having a preferential binding affinity for the labeled anti-digoxin antibody which is therefore capable of complexing with the labeled substance. The solid phase material is of such physical characteristics that is can be easily dispersed in the reaction mixture and settled out. Therefore the density and overall size of the solid phase material is such that a rapid dispersal by agitation and sediment by gravity is facilitated.

The solid phase material is present as a particle or matrix having a density greater than water. The solid phase material has a sedimentation rate in water of from about 5 seconds per centimeter to about 2 minutes per centimeter, more preferably from about 20 seconds per centimeter to about 1.5 minutes per centimeter. The size of particle which forms the solid phase material can be from about 5 microns to about 300 microns, preferably from about 40 microns to about 160 microns in diameter. The sedimentation rate and size is important to assuring the solid phase material both disperses and settles readily without significant input of energy or motion to the reaction vessel containing the subject reaction mixture. This is especially important when employing an automated diagnostic apparatus.

The solid phase material can be fabricated from any number of synthetic materials. Preferably the solid phase material is manufactured from polymeric materials such as agarose, polystyrene, polyacrylamide, their derivatives or mixtures thereof. Generally the solid phase is present as bead-like structures. Most preferably, Trisacryl ® beads are employed. The solid phase material can be delivered to the reaction vessel as a dry powder, wet slurry, tablet or a capsule. To facilitate handling, speed dissolution and maximize stability, solid phase material in tablet form is preferred.

In the preferred assay, the labeled anti-digoxin antibody is affinity purified on a affinity column containing 1,11,19 tris(acetyloxy)-3-[(6-deoxy-L-mannopyranosyl) oxy]5,14 dihydroxycard-20(22)-enolide, (1β,3β,5β,11) using well known procedures in Dean et al. ¢Affinity Chromotography" (IRL Press Limited 1985).

Immobilized on the solid phase material is a compound having a preferential binding affinity for the labeled anti-digoxin antibody. This compound is complimentary to the substance to be identified, in this case digoxin, and is capable of complexing the labeled substance. The complex formed is bonded to the solid phase material and because of its physical characteristics settles out or sediments by gravity. The compound can be directly bonded to the solid phase or covalently bonded through a linkage group such as a protein, or an organic spacer arm. The total reaction mixture thus becomes separated into a solid phase containing the solid phase material complexed with any excess labeled substance and a liquid phase containing the material sought to be quantified which is complexed to the labeled substance.

An important aspect of this invention is that the compound immobilized must exhibit sufficient binding affinity for the labeled substance when bound to the solid phase material and must also possess poor recognition for the labeled substance when disassociated from the solid phase material. Surprisingly, this combination of adequate binding affinity and poor recognition of anti-digoxin antibodies is exhibited by compounds according to structural Formula I herein.

In the preferred embodiment of the invention the ouabain triacetate compounds of Formula I serve as the immobilized compound. In the most preferred embodiment of the invention the ouabain triacetate compound is 1,11,19-tris(acetyloxy)-3-[(6-deoxy-α-L-mannopyranosyl) oxy]-5,14 dihydroxycard-20(22)-enolide, (1β,3β,5β,11α) (Formula II herein) and is bonded to the solid phase material through a protein linker arm. This compound is most preferred based on its low affinity (See Example III). It is to be understood that while the above-named ouabain triacetate derivative synthesized in accordance with the procedure in Example I herein is the preferred compound for immobilization on the solid phase material, the procedures set forth in Example I can be altered in ways known by those of skill in the art to produce other useful ouabain triacetate compounds such as those represented by structural Formula I.

Subsequent to removal of the excess labeled substance with solid phase material/immobilized compound complex, the liquid phase is then measured for amount of the material sought to be quantified, e.g. digoxin. Generally, this is accomplished by extracting the liquid phase by syringe, suction, or other means. An appropriate immunoassay format is then employed to measure the amount of labeled substance consistent with the particular label employed.

Typical labeling means can include enzymes, radioisotopes, chromophores, fluorophores or any substance which is capable of generating a detectable signal, either alone or in combination with other reagents. Procedures and methods for labeling and identifying the labeled complexes are well known in the art of diagnostic immunoassay as is generally discussed in L. Miles and C. Hales, *Labeled Antibodies and Immunological Assay Systems*, Nature 219, 187–189 (1968) and U.S. Pat. No. 3,654,090. In the preferred digoxin assay the lable is beta-galactosidase.

The subject method is especially useful in an automated diagnostic immunoassay apparatus because of its relatively automatic purification of the complex to be measured. Particularly, the immunoassay method can be conducted by mixing the biological fluid to be analyzed for digoxin with sufficient labeled substance and then adding this reaction mixture to a vessel containing the subject solid phase material or adding the subject solid phase material to the initial reaction mixture wherein the subject solid phase material purifies the reaction mixture of excess labeled substance without requiring additional physical or chemical treatment steps. Thus, the subject method avoids the necessity to centrifuge, prepare an elute from a column, or employ other more tedious steps to obtain the labeled substance for final measurement.

Preferably, the present invention is directed to noncompetitive assay procedures, as described above and in Example 4. However, the present invention also envisions competitive assay techniques. In the competitive assay format measurement of digoxin in a sample fluid involves simultaneous incubation of β-galactosidase-labeled F(ab')₂ antibody fragments with sample and a ouabain triacetate-albumin-trisacryl solid phase. The solid phase material and the β-galactosidase-labeled F(ab')₂ compete for analyte. Following the competitive reaction period the solid phase sediments and an aliquot containing analyte β-galactosidase labeled F(ab')₂ is transfered to a cuvette for quantitation using a fluorogenic substrate.

EXAMPLE I

A. Preparation of Ouabain Triacetate

OUABAIN HEXA-ACETATE

A mixture of 4.7g (6.45 mmoles) of ouabain octahydrate and 400 mg (3.28 mmoles) of 4-dimethylaminopyridine was dissolved in 95 ml of 1:4 acetic anhydride in pyridine and stirred overnight. The clear yellow solution was diluted with 200 ml of methylene chloride, then extracted with ice cold 25% aqueous sulfuric acid until the aqueous phase remained acidic. The organic phase was then washed with water, brine, and dried on sodium sulphate. Filtration and solvent removal yielded 5.3 g (98%) of product as a yellow solid, which was used without further purification. TLC on silica gel with 20% methanol in methylene chloride gave the following $R_f$ values: ouabain=0.11, and ouabain hexa-acetate=0.87.

OUABAIN TRI-ACETATE (PROCEDURE I)

A mixture of ouabain hexa acetate (1.02 g, 1.22 mmoles) and potassium cyanide (75 mg, 1.15 mmoles) in 15 ml of methanol was stirred at room temperature. The solid hexa-acetate was only slightly soluble in methanol. However all material was dissolved after about 1.5 hr of stirring. After 6 hours approximately 5 g of silica gel was added to the reaction mixture, and the solvent was removed by rotary evaporation. It is important that the temperature be kept below 45° C. during this step. This silica gel was placed on a flash chromatography column and eluted with 10% methanol in methylene chloride. Fractions corresponding to the major product were pooled and the solvent removed to yield 841 mg (97%) of product as a glassy solid, which yielded a white powder when scraped from the sides of the flask. Evaluation of the product by NMR and mass spectrometry showed it to be 1,11,19 -tris(acetyloxy)-3-[(6-deoxy-α-L-mannopyranosyl)oxy]-5,14 dihydroxycard-20(22)-enolide (1β,3β,5β,11α). TLC on silica gel (20% methanol/methylene chloride) gave an $R_f$ of 0.49 for ouabain tri-acetate.

OUABAIN TRI ACETATE (PROCEDURE 2)

A mixture of ouabain hexa-acetate (10.0 g, 12.0 mmoles), and potassium carbonate (0.75 g, 5.4 mmoles) in 250 ml of methanol was stirred at room temperature. After 0.5 hr the reaction mixture was filtered, and dilute aqueous acetic acid was added to the filtrate until a 0.25 ml aliquot dissolved in 2 ml of water gave a neutral pH. Fifty grams of silica gel was then added to the reaction mixture, and the solvent was removed by rotary evaporation. The dry silica gel was then placed on a flash chromatography column and eluted with 15% methanol in methylene chloride. The fractions corresponding to the major product were pooled and the solvent removed to yield 8.5 g of product (89%) as a white solid. Evaluation of the product by NMR and mass spectrometry showed it to be 1,11,19-tris(acetyloxy)-3-[(6-deoxy-α-L-mannopyranosyl)oxy]-5,14 dihydroxycard 20(22)-enolide (1β,3β,5β,11α). TLC on silica gel (20% methanol/methylene chloride) gave an $R_f$ of 0.49 for ouabain tri-acetate.

B. Preparation of Affinity Purified F(ab')₂ Fragments

Rabbit antiserum directed against digoxin was fractionated by $(NH_4)_2SO_4$ precipitation and reacted with pepsin to produce F(ab')₂ fragments. The F(ab')₂ fragments were purified by affinity chromatography on Trisacryl bovine serum albumin-ouabain triacetate using the general procedures in Dean et al. "Affinity Chromatography" (IRL Press Limited 1985).

EXAMPLE II

A. Preparation of β-galactosidase labeled F(ab')₂ Fragments

Affinity purified F(ab')₂ fragments were coupled to β-galactosidase using essentially the methodology described for attaching IgG molecules to β-galactosidase in Kang et al., Clin. Chem. 32:1682 (1986). F(ab')₂-β-galactosidase conjugates were isolated by size exclusion chromatography using a Superose ™ 6 column.

B. Preparation of Solid Phases

Ouabain, ouabain triacetate 1,11,19-tris(acetyloxy)-3-[(6-deoxy-α-L-mannopyranosyl)oxy]-5,14 dihydroxy-card 20(22) enolide ($1\beta,3\beta,5\beta,11\alpha$) and digoxin solid phases were prepared in a similar manner. Ouabain triacetate, ouabain and digoxin were attached to bovine serum albumin following the general scheme described in Biochemistry 9:331 (1970). The albumin conjugates were subsequently coupled to Trisacryl® previously activated with carbonyl diimidazole in a manner similar to that described by Bethell, J. Biol. Chem., 254:2572 (1979).

EXAMPLE III

A. Antigenicity of Cardiac Glycoside Analogs

The antigencity of cardiac glycoside analogs was first determined using the TDx@ analyzer and the Abbott Digoxin II assay commercially available from Abbott Laboratories, Abbott Park, Ill. 60064. Analogs were evaluated as aqueous solutions in TDx dilution buffer. Several analogs were also subsequently evaluated using the new digoxin assay described herein (see generally Example IV) using a ouabain triacetate solid phase prepared in accordance with Example IIB. Analogs evaluated were:

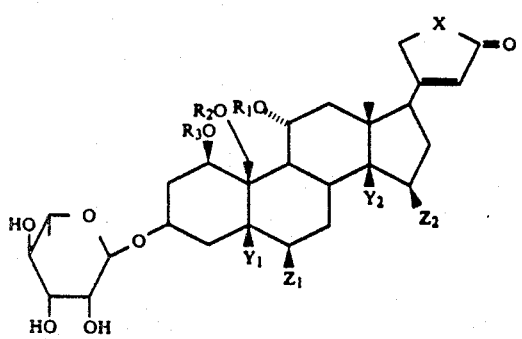

wherein $R_1=R_2=R_3=Ac$, $X=O$, $Y_1$, $Z_1$ and $Y_2$, $Z_2=$ a bond connecting the two carbon atoms-to which they are attached (A); $R_1=R_2=R_3=Ac$, $X=O$, $Y_1=OH$. $Z_1=H$, $Y_2$ and $Z_2=$ a bond connecting the two carbon atoms to which they are attached (B); $R_1=R_2=R_3=Ac$, $X=O$, $Y_1=Y_2=OH$, $Z_1=Z_2=H$ (C); and $R_1=R_2=R_3=H$, $X=N$, $Y_1=Y_2=OH$, $Z_1=Z_2=H$ (D). Cross-reactivity was defined as the observed assay concentration divided by the actual analog concentration times 100.

| ANALOG | CROSS-REACTIVITY (%) | |
|---|---|---|
| | DIGOXIN II | NEW ASSAY |
| Digoxin | 100 | 100 |
| Digoxin Lactam | 0.41 | — |
| Ouabain | $2.0 \times 10^{-2}$ | $1.8 \times 10^{-3}$ |
| Ouabain Triacetate (A) | $1.6 \times 10^{-3}$ | — |
| Ouabain Triacetate (B) | $1.5 \times 10^{-3}$ | — |
| Ouabain Lactam (D) | $9.1 \times 10^{-4}$ | — |
| Ouabain Triacetate (C) | $3.7 \times 10^{-4}$ | $2.2 \times 10^{-4}$ |

EXAMPLE IV

A. Non-Competitive Assay for the Measurement of Digoxin in a Sample Fluid Utilizing Immobilized Ouabain Triacetate Solid Phase Material The general assay format consists of preincubation of excess β-galactosidase labeled F(ab')₂ (Example II A) with sample such that sample is quantitatively and rapidly bound to form an analyte β-galactosidase labeled F(ab')₂ conjugate. An aliquot of this mixture is transferred to a vessel containing a ouabain triacetate albumin-trisacryl solid phase prepared in accordance with procedure of Example II B and having a characteristic density to be easily suspended in solution yet sufficiently dense to rapidly sediment by gravity. The solid phase material rapidly captures the excess unconjugated β-galactosidase-labeled F(ab')₂ and sediments. Following the capture reaction and sedimentation an aliquot containing analyte-β-galactosidase labeled F(ab')₂ is transfered to a cuvette for quantitation using a fluorogenic substrate.

Serum solutions containing 0, 0.5, 1.0, 2.0, 3.0 and 5.0 nanograms per milliliter of digoxin were each tested following the same assay protocol described below. A control was also run with zero digoxin and no solid phase material. Fifty microliters of serum sample was mixed with 25 microliters of the β-galactosidase-labeled F(ab')₂ (Example II A) and 325 microliters of TDx dilution buffer. The reaction mixture was incubated at 34–35 degrees Celsius for 6 minutes and then a 60 microliter aliquot and 55 microliters of TDx dilution buffer was added to 10 mg of solid phase material (Example II B). The mixture was incubated for 10 minutes with mixing. 400 ul of TDx dilution buffer was then added to the mixture.

The mixture was allowed to rest briefly whereupon it separated into a liquid and solid phase. The β-galactosidase activity of the supernatant was measured by quantitating the production of fluorescein. The measurement was made using 10 micromolar di-(β-D-qalactosyl) fluorescein as substrate in TDx dilution buffer containing 1 mM $MgCl_2$. The measurements were as follows:

| Test No. | Concentration Digoxin (Nanograms/mL) | Fluorescence Measured Rate |
|---|---|---|
| Control (no solid phase material) | 0.0 | 1803 |
| 1 | 0.0 | 123 |
| 2 | 0.5 | 160 |
| 3 | 1.0 | 220 |
| 4 | 2.0 | 448 |
| 5 | 3.0 | 745 |
| 6 | 5.0 | 1231 |

The measurement obtained show that by employing the subject method a standard curve can be made to analyze serum dilutions containing unknown digoxin concentrations. Also, the zero concentration measurement as compared to the control shows that the excess antibody conjugate was effectively removed by the subject method.

EXAMPLE V

Comparative selection of F(ab')$_2$ by Affinity Chromatography Using Ouabain and Ouabain Triacetate F(ab')$_2$ fragments were affinity purified using either an ouabain triacetate or ouabain solid phase matrix using the procedure described in Example I B. β-Galactosidase labeled conjugates were made using each of these type of F(ab')$_2$ fragments as described in Example II A. Each type of conjugate was tested for its capacity to bind a ouabain triacetate solid phase. The results are as follows:

|  | Ouabain F(ab')$_2$ | Ouabain Triacetate F(ab')$_2$ |
|---|---|---|
| Control (Rate) + | 1686 | 1821 |
| Solid Phase (Rate) | 373 | 168 |
| % Bound | 78 | 91 |

As the table above indicates affinity selection of F(ab')$_2$ fragments using the ouabain triacetate matrix provides a conjugate giving higher binding and therefore superior assay performance.

EXAMPLE VI

Use of a Low Affinity Analyte as the Solid Phase Ligand

A. Stability/Lyophilization

The enhanced stability derived from using a low affinity analyte as a solid phase ligand was analyzed in several ways. In the first instance, two different types of solid phase, one made with digoxin and one made with ouabain triacetate 1,11,19-tris(acetyloxy)-3-[(6-deoxy-α-L-mannopyranosyl)oxy]-5,14 dihydroxycard-20(22)-enolide (1β,3β,5β,11α) were evaluated for their stability to lyophilization. The two lyophilized solid phases were then evaluated for longer term stability. The data is shown below.

|  | Digoxin Solid Phase | Ouabain Triacetate Solid Phase |
|---|---|---|
| Pre-lyophilization (Binding %) | 79 | 96 |
| Post-lyophilization (Binding, %) | 61 | 95 |
| Decrease (%) | 23% | 1% |

B. Stability/Storage of Lyophilized Solid Phase

Each above lyophilized solid phase used was stored at room temperature and evaluated for its ability to bind antibody enzyme as a function of time. The results observed were as follows:

|  | Binding (%) | |
|---|---|---|
| Days | Digoxin | Ouabain Triacetate |
| 0 | 60 | 96 |
| 3 | 48 | — |
| 6 | 30 | — |
| 30 | — | 96 |

As the results show, the digoxin solid phase loses its binding capacity quickly when stored at room temperature. The ouabain triacetate solid phase was stable over this same time period.

C. Binding To Solid Phase/Leaching

Ouabain and Ouabain Triacetate 1,11,19-tris-(acetyloxy)-3-[(6-deoxy-α-L-mannopyranosyl)oxy]-5,14 dihydroxycard-20(22)-enolide 1β,3β,5β,11α) were attached to albumin and then Trisacryl ® using similar chemistry such that leaching due to bond breaking should occur similarly in both solid phases. Trypsin was used to digest the albumin linker arm, thereby accelerating this leaching rate. Trypsin had the important advantage of not changing the structure of either analyte which could occur with many non-enzymatic methods. The experimental results are as follows:

% Binding of Antibody-Enzyme Conjugate to Solid Phases

|  | Ouabain | Ouabain Triacetate |
|---|---|---|
| No Trypsin | 88 | 88 |
| Trypsin, (.2 mg/ml), (10 minutes) | 28 | 45 |
| Trypsin, (.2 mg/ml), (30 minutes) | 10 | 28 |

The leaching of ouabain clearly is more detrimental to antibody enzyme binding and therefore assay performance than the leaching of ouabain triacetate. This is predicted due to the vastly different cross-reactivities of equimolar amounts of ouabain and ouabain triacetate. (See Example III).

We claim:

1. A compound of the formula:

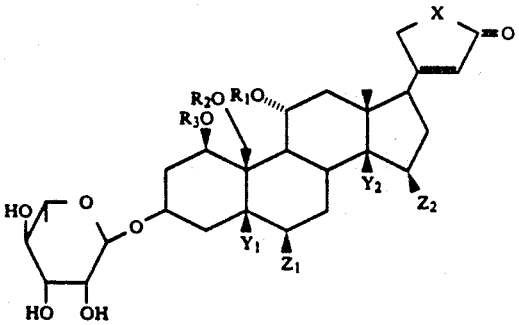

wherein $R_1=R_2=R_3'$Ac, X=O, $Y_1=Y_2$=OH, $Z_1=Z_2$=H; or $R_1=R_2=R_3$=Ac, X=O, $Y_1$=OH, $Z_1$=H, $Y_2$ and $Z_2$= a bond connecting the two carbon atoms to which they are attached; or $R_1=R_2=R_3$=Ac, X=O, $Y_1,Z_1$ and $Y_2,Z_2$= a bond connecting the two carbon atoms to which they are attached; or $R_1=R_2=R_3$=H, X=N, $Y_1=Y_2$=OH, $Z_1=Z_2$=H.

2. The compound of claim 1 wherein:
$R_1=R_2=R_3$=Ac, X=O, $Y_1=Y_2$=OH, $Z_1=Z_2$=H.

* * * * *